United States Patent [19]

Schneider et al.

[11] 4,105,797

[45] Aug. 8, 1978

[54] FUNGICIDAL 3-AMINO-6-TRIFLUOROMETHYL-2,4-DINITRODIPHENYLETHERS

[75] Inventors: Louis Schneider, Elizabeth; David E. Graham, Westfield, both of N.J.

[73] Assignee: GAF Corporation, New York, N.Y.

[21] Appl. No.: 759,258

[22] Filed: Jan. 14, 1977

[51] Int. Cl.$^2$ .................. A01N 9/20; A01N 9/24; C07C 91/16; C07C 91/28
[52] U.S. Cl. ................................ 424/330; 260/571
[58] Field of Search ............... 424/330, 340; 260/568, 260/571, 612 R

[56] References Cited

U.S. PATENT DOCUMENTS

| | | | |
|---|---|---|---|
| 3,322,525 | 5/1967 | Martin et al. | 260/612 R |
| 3,423,470 | 1/1969 | Rohr et al. | 260/612 R |
| 3,558,720 | 1/1971 | Schmidt-Collerus et al. | 260/612 R |
| 3,647,888 | 3/1972 | Rohr et al. | 424/340 |
| 3,908,019 | 9/1975 | Noguchi et al. | 424/340 |
| 3,914,310 | 10/1975 | Frick et al. | 260/571 |
| 3,929,903 | 12/1975 | Noguchi et al. | 424/340 |
| 3,950,377 | 4/1976 | Barlow | 424/330 |

FOREIGN PATENT DOCUMENTS 1,542,326  6/1967  France ................. 424/340

*Primary Examiner*—Albert T. Meyers
*Assistant Examiner*—D. W. Robinson

*Attorney, Agent, or Firm*—Walter C. Kehm; Walter Katz

[57] ABSTRACT

Fungicidal 3-amino-6-trifluoromethyl-2,4-dinitrodiphenylethers having the formula:

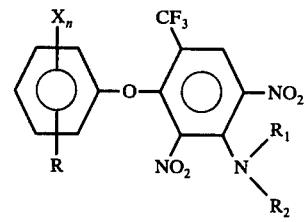

where
R is H or lower alkyl,
X is halogen,
$n$ is 0, 1, 2 or 3, and
$R_1$ and $R_2$ are selected from H and lower alkyl, or form a piperidinyl, morpholinyl, or pyrrolidinyl ring structure, are prepared by two-step process involving reaction of 2,4-dichloro-3,5-dinitrotrifluoromethylbenzene with an amine, and condensation of the intermediate with a phenol.

The compounds of the invention show good fungicidal activity against bean mildew, bean rust and tomato blight, and insecticidal activity against Mexican bean beetle.

12 Claims, No Drawings

FUNGICIDAL 3-AMINO-6-TRIFLUOROMETHYL-2,4-DINITRODIPHENYLETHERS

BACKGROUND OF THE DISCLOSURE

1. Field of the Invention

This invention relates to a class of fungicides which are effective for many agricultural uses.

2. Description of the Prior Art

Diphenylether compounds are known in the art as being useful agricultural chemicals. Accordingly, it is the object of this invention to provide new and useful diphenylethers which exhibit good fungicidal activity.

SUMMARY OF THE INVENTION

The present invention provides fungicidal 3-amino-6-trifluoromethyl-2,4-dinitrodiphenylethers having the formula:

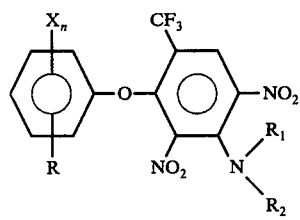

where
  R is H or lower alkyl,
  X is halogen,
  $n$ is 0, 1, 2 or 3, and
  $R_1$ and $R_2$ are selected from H and lower alkyl, or form a piperidinyl, morpholinyl, or pyrrolidinyl ring structure.

The compounds of the invention are prepared by two-step process involving reaction of 2,4-dichloro-3,5-dinitrotrifluoromethylbenzene with an amine, and condensation of the intermediate with a phenol.

The products described herein exhibit fungicidal activity against bean mildew, bean rust and tomato blight, and insecticidal activity against Mexican bean beetle.

DESCRIPTION OF THE PREFERRED EMBODIMENTS

The compounds of this invention are prepared by condensing a substituted-phenyl halide (I) with a phenol (II) to produce the desired substituted-diphenylether (III), as follows:

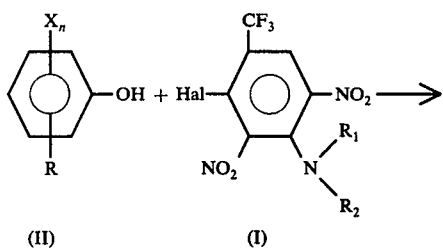

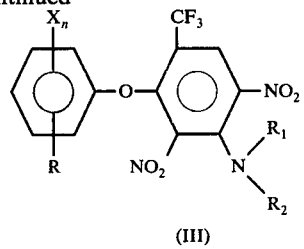

where Hal is a halogen.

The presence of the nitro and trifluoromethyl groups adjacent the halogen substituent on starting material I activates the halogen position on the ring so that condensation with the phenol reactant II takes place at the desired position of the benzene ring. The condensation reaction proceeds by nucleophilic displacement of the halogen atom by a phenoxy group to produce the desired substituted-diphenylether III.

Intermediate I is produced by a two-step process. The first step involves dinitration of the corresponding dihalo compound IV to produce the dinitro compound IV to produce the dinitro compound V. In the second step V is aminated to provide the desired intermediate I.

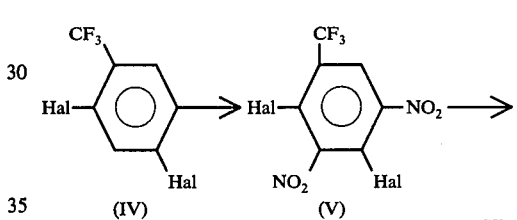

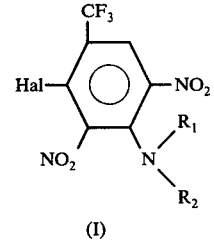

Dinitration is conducted in a mixture of nitric and sulfuric acids, as described in U.S. Pat. No. 3,586,725. Precurser IV is commercially available from the Hooker Chemical Co., Buffalo, N.Y.

The amination step may be carried out by reacting V with an amine in a suitable solvent such as an alcohol, preferably in the presence of an acid acceptor, which may be an excess of the amine itself, as described in the aforementioned patent.

The reaction of intermediate I with the phenol reactant to produce III is carried out by stirring the reactants in a basic medium for an extended period of time at room temperature, in a suitable solvent, such as acetone. The dilute alkali serves as an acceptor for the hydrogen halide which is released during the reaction.

Suitable alkaline compounds useful for this reaction include an alkali metal hydroxide or carbonate, such as sodium hydroxide, sodium carbonate, potassium carbonate, and the like. Upon completion of the reaction, the alkali halide is filtered off and the acetone is removed by roto-evaporation. The remaining product then is recrystallized from a suitable solvent, such as methanol.

The compounds of the invention are useful as agricultural fungicides when applied to the soil at the rate of about 1 to 25 lbs. per acre or as a foliar spray at concentrations of about 31 to 260 ppm. They show foliar fungicidal activity against the following pathogens: early blight of tomatoes, bean mildew, bean rust, and insecticidal activity against Mexican bean beetle.

The materials of the present invention may be applied to those fungus susceptible plants on site at a rate of about 1 or less to about 25 pounds per acre depending on various circumstances of the susceptibility to the fungus, the weather, the stage of growth and various other factors. The material may be applied as a dust or spray. As a dust it is more practical to extend it with diluents such as bentonite, chalk, clay, diatomaceous earth, fullers earth, mica, ground slate or any of the other usual carriers for agricultural chemicals. As a spray it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the fungus.

Following are examples of preparation of the compounds of the invention, and are presented by way of illustration and are not intended to be limiting unless otherwise specified.

EXAMPLE 1

3-Diethylamino-6-Trifluoromethyl-2,4-Dinitrodiphenylether

2-Chloro-4-diethylamino-3,5-dinitrotrifluoromethylbenzene (34.2 g., 0.1 mole), phenol (9.4 g., 0.1 mole), potassium carbonate (13.8 g., 0.1 mole), and acetone (100 ml.) were charged into 250 cc 4-neck flask equipped with a stirrer, condenser, thermometer and a drying tube. The reaction mixture was stirred for 18 hrs. at 50° C. Potassium chloride (6 g.) was filtered off and the acetone removed by roto-evaporation. The residue was crystallized twice from methanol yielding 24 g. (60%) of product, m.p. 70°–71° C., glc. 99%.

Anal. Calcd for $C_{17}H_{16}F_3N_3O_5$: N, 10.52. Found: N, 10.46.

EXAMPLE 2

3-Diethylamino-6-Trifluoromethyl-2,4-Dinitro-3'-Methyldiphenylether

2-Chloro-4-diethylamino-3,5-dinitrotrifluoromethylbenzene (34.2 g., 0.1 mole), m-cresol (12.0 g., 0.11 mole), potassium carbonate (16.0 g., 0.11 mole), and acetone (175 ml.) were reacted and worked up as in Example 1 to yield 30 g. of product, (72.5%) m.p. 63.5°–64.5° C., glc. 99%.

Anal. Calcd for $C_{18}H_{18}F_3N_3O_5$: N, 10.16. Found: N, 10.12.

EXAMPLE 3

3-sec-Butylamino-6-Trifluoromethyl-2,4-Dinitrodiphenylether 4-sec-Butylamino-2-chloro-3,5-dinitrotrifluoromethylbenzene (34.2 g., 0.1 mole), phenol (9.4 g., 0.1 mole), potassium carbonate (15.2 g., 0.11 mole), and acetone (100 ml.) were reacted and worked up as in Example 1 to yield 23 g. (55.6%) of product, m.p. 110°–112° C., glc. 98%.

Anal. Calcd for $C_{17}H_{16}F_3N_3O_5$: N, 10.52. Found: N, 10.28.

EXAMPLE 4

3-sec-Butylamino-6-Trifluoromethyl-2,4-Dinitro-3'-Methyldiphenylether 4-sec-Butylamino-2-chloro-3,5-dinitrotrifluoromethylbenzene (17.1 g., 0.05 mole), m-cresol (5.4 g., 0.5 mole) potassium carbonate (7.6 g., 0.055 mole) and acetone (50 ml.) were reacted for 18 hours at 25° C to yield 13 g. (59.6%) of crude product which was recrystallized from methanol, m.p. 25°, glc. 98%.

Anal. Calcd for $C_{18}H_{18}F_3N_3O_5$: N, 10.16 Found: N, 9.93.

EXAMPLE 5

3-sec-Butylamino-6-Trifluoromethyl-2,4-Dinitro-2',4',5'-Trichloro-Diphenylether 4-sec-Butylamino-2-chloro-3,5-dinitrotrifluoromethylbenzene (34.2 g., 0.1 mole), 2,4,5-trichlorophenol, (19.72 g., 0.1 mole) potassium carbonate (15.2 g., 0.11 mole) and acetone (100 ml.) were reacted and worked up as in Example I to yield 28.0 (53.2%) of product, which was recrystallized twice from methanol, m.p. 121°–122° C, glc. 98%.

Anal. Calcd for $C_{17}H_{13}Cl_3F_3O_5N_3$: N, 8.37; Cl, 21.21; Found: N, 8.37; Cl, 21.09.

EXAMPLE 6

3-Diethylamino-6-Trifluoromethyl-2,4-Dinitro-4'-Chlorodiphenylether and 3-Diethylamino-6-Trifluoromethyl-2,4-Dinitro-2',4'-Dichlorodiphenylether The procedure of Example 1 is followed using 4-chlorophenol and 2,4-dichlorophenol in place of phenol to produce the corresponding 3-diethylamino-6-trifluoromethyl-2,4-dinitro-4'-chlorodiphenylether, m.p. 90°–91° C (81%), % N: Calcd. 9.67, Found 9.70. % Cl: Calcd: 8.17, Found 8.20; and 3-diethylamino-6-trifluoromethyl-2,4-dinitro-2',4'-dichlorodiphenylether, m.p. 84°–86° C. (77%); % N: Calcd: 8.97, Found: 8.68; % Cl: Calcd: 15.2, Found: 15.6.

EXAMPLE 7

3-sec-Butylamino-6-Trifluoromethyl-2,4-Dinitro-4'-Chlorodiphenylether and 3-sec-Butylamino-6-Trifluoromethyl-2,4-Dinitro-2',4'-Dichlorodiphenylether The procedure of Example 3 is followed using 4-chlorophenol and 2,4-dichlorophenol in place of phenol to produce the corresponding 3-sec. butylamino-6-trifluoromethyl-2,4-dinitro-4'-chlorodiphenylether, m.p. 61°–62° C, (61%), % N: Calcd. 9.66, Found 9.67; % Cl: Calcd: 8.16, Found 8.08; and 3-sec-butylamino-6-trifluoromethyl-2,4'-dinitro-2',4'-dichloro diphenylether, m.p. 84°–85° C, (81%), % N: Calcd: 8.97, Found: 9.12; % Cl: Calcd: 15.2, Found: 14.9.

EXAMPLE 8

The procedures of the above Examples are repeated using morpholine, piperidine and pyrrolidine in place of diethylamine or sec-butylamine to produce the corresponding 3-morpholino, 3-piperidinyl and 3-pyrrolidinyl-6-trifluoromethyl-2,4-dinitrodiphenylether;  -6-trifluoromethyl-2,4-dinitro-3'-methyldiphenylether;-6-trifluoromethyl-2,4-dinitro-4'chlorodiphenylether;-6-trifluoromethyl-2,4-dinitro-2',4'-dichlorodiphenylether; and -6-trifluoromethyl-2,4-dinitro-2',4',5'-trichlorodiphenylether compounds.

EXAMPLE 9

FOLIAGE FUNGICIDE TESTS

The product of Example 2 was tested on tomato early blight as follows: Young tomato seedlings 4 to 5 weeks of age were atomized while rotating on a turntable with a suspension of the test material diluted to 125,63 and 31 ppm. After the deposit dried, the plants were atomized with a spore suspension and incubated in a humidity cabinet at 70° to 75° F for 24 hours. Then they are held in a greenhouse until lesions appear (usually 2 to 3 days). The severity of infection is rated on a scale of 0 (no reduction) to 10 (complete elimination of infection.) The results versus the standard Maneb, manganese ethyl bis-dithiocarbamate, are as follows:

| Conc., ppm | Fungitoxicity Rating | |
|---|---|---|
| | Compound of Ex. 2 | Maneb |
| 125 | 8.0 | 10.0 |
| 62 | 6.5 | 9.1 |
| 31 | 6.5 | 9.1 |

EXAMPLE 10

The product of Example 1 was tested on bean powdery mildew as follows: Healthy young bean plants with fully expanded primary leaves in 2½ inch pots were placed for 2 days on a greenhouse bench between two rows of infected plants covered with a mass of white, powdery conidia so that they were exposed to a shower of conidia.

The primary test plants with incipient infection were atomized while rotating on a turntable with a suspension of 250 ppm of a test material. The treated plants were then returned to the greenhouse bench near infected plants. After 7 days preliminary observations were made on the eradication of established infection present on the primary leaves at the time of spraying. The plants were reexamined 7 days later for infection on new growth as well as on the primary leaves to determine residual and systemic effects on the fungus. On both dates the leaves were rated on a scale of 0 (no suppression) to 10 (complete eradication or prevention of infection), and compared to the commercial standard Karathane, 2,4-dinitro-6-octylphenylcrotonate.

| conc., ppm | Fungitoxicity Rating | |
|---|---|---|
| | Compound of Ex. 1 | Karathane |
| 250 | 9.0 | 10 |

EXAMPLE 11

The product of Example 3 was tested on bean rust as follows: Pinto beans grown in 2.5 inch pots for 9 to 12 days is sprayed while plants are rotating on a turntable with 100 ml. of a formulation at 250 ppm. After the spray deposit dries, plants are placed in a moist chamber at 70° F. for 24 hours. After 7 to 9 days the severity of pustule formation is rated as in Example 8 and compared with the commercial standard Plantvax, 2,3-dihydro-5-carbanilido-6-methyl-1,4-oxathiin-4,4-dioxide.

| Conc., ppm | Fungitoxicity Rating | |
|---|---|---|
| | Compound of Ex. 3 | Plantvax |
| 250 | 8.0 | 9.0 |

EXAMPLE 12

The product of Example 4 was tested for insecticidal activity against Mexican bean beetle as follows: a combination of stomach poison and feeding deterrent effects was measured on larvae of the Mexican bean beetle about 5 to 7 days after their emerging from eggs. Leaves of young bean plants were removed from the plants by cutting the petioles and were dipped in a suspension of the chemical at 250 ppm in the primary tests. Petioles of the excised leaves were placed in a water reservoir to maintain leaf turgidity and 5 larvae were placed upon them as soon as the chemical deposit was dry. Observations were made on the mortality of the beetles and the extent of inhibition of feeding 2 or 3 days later. The two responses were rated 0 (no effect on mortality or feeding) to 10 (complete destruction of larvae and total inhibition of feeding). Leaves dipped in Azodrin is O,O-dimethyl-O-(2-methyl carbamoyl-1-methylvinyl) phosphate.

| Conc., ppm | Insecticidal Activity | |
|---|---|---|
| | Compound of Ex. 4 | Azodrin |
| 250 | 10 | 10 |

While the invention has been described with particular reference to certain embodiments thereof, it will be understood that certain modifications and changes may be made which are within the skill of the art. Therefore it is intended to be bound only by the appended claims.

What is claimed is:

1. A compound of the formula:

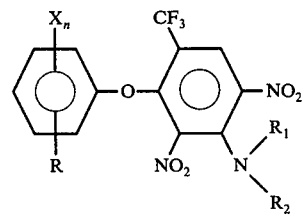

where
R is H or lower alkyl,
X is halogen,
$n$ is 0, 1, 2 or 3, and
$R_1$ and $R_2$ are selected from H and lower alkyl.

2. 3-Diethylamino-6-trifluoromethyl-2,4-dinitrodiphenylether, which is a compound of claim 1.

3. 3-Diethylamino-6-trifluoromethyl-2,4-dinitro-3'-methyldiphenylether, which is a compound of claim 1.

4. 3-sec-Butylamino-6-trifluoromethyl-2,4-dinitrodiphenylether, which is a compound of claim 1.

5. 3-sec-Butylamino-6-trifluoromethyl-2,4-dinitro-3'-methyldiphenylether, which is a compound of claim 1.

6. 3-sec-Butylamino-6-trifluoromethyl-2,4-dinitro-2',4',5'-trichlorodiphenylether, which is a compound of claim 1.

7. 3-Diethylamino-6-trifluoromethyl-2,4-dinitro-4'-chlorodiphenylether, which is a compound of claim 1.

8. 3-Diethylamino-6-trifluoromethyl-2,4-dinitro-2',4'-dichlorodiphenylether, which is a compound of claim 1.

9. 3-sec-Butylamino-6-trifluoromethyl-2,4-dinitro-4'-chlorodiphenylether, which is a compound of claim 1.

10. 3-sec-Butylamino-6-trifluoromethyl-2,4-dinitro-2',4'-dichlorodiphenylether, which is a compound of claim 1.

11. A method of controlling undesired fungi comprising applying thereto a fungicidally effective amount of a compound of the formula:

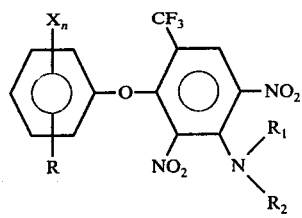

where
R is H or lower alkyl,
X is halogen,
$n$ is 0, 1, 2 or 3, and
$R_1$ and $R_2$ are selected from H and lower alkyl.

12. A fungicidal composition comprising:
(a) a fungicidally effective amount of a compound of the formula:

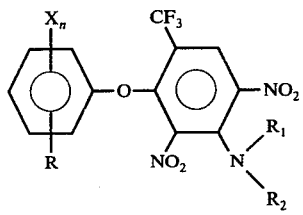

where
R is H or lower alkyl,
X is halogen,
$n$ is 0, 1, 2 or 3, and
$R_1$ and $R_2$ are selected from H and lower alkyl, and
(b) an agriculturally acceptable inert carrier.

* * * * *